(12) United States Patent
Nishina et al.

(10) Patent No.: US 8,211,007 B2
(45) Date of Patent: Jul. 3, 2012

(54) LYMPH NODE REMOVING METHOD

(75) Inventors: Kenichi Nishina, Hachioji (JP);
Shinichi Tsutaki, Hachioji (JP);
Takeharu Nakazato, Koganei (JP);
Tetsuya Yamamoto, Hanno (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/217,770

(22) Filed: Aug. 25, 2011

(65) Prior Publication Data
US 2011/0313246 A1    Dec. 22, 2011

Related U.S. Application Data

(62) Division of application No. 12/120,831, filed on May 15, 2008.

(51) Int. Cl.
*A61B 1/00* (2006.01)

(52) U.S. Cl. ........ 600/104; 600/114; 600/564; 600/567; 604/44

(58) Field of Classification Search ................... 600/104, 600/562, 564, 567; 606/44, 185, 222–223
See application file for complete search history.

(56) References Cited

U.S. PATENT DOCUMENTS

| | | | |
|---|---|---|---|
| 4,235,238 A | | 11/1980 | Ogiu et al. |
| 4,874,375 A | * | 10/1989 | Ellison ................... 604/164.01 |
| 5,823,971 A | * | 10/1998 | Robinson et al. ............. 600/567 |
| 6,171,249 B1 | | 1/2001 | Chin et al. |
| 6,179,860 B1 | * | 1/2001 | Fulton et al. ................. 606/200 |
| 6,200,313 B1 | | 3/2001 | Abe et al. |

| | | | |
|---|---|---|---|
| 2004/0249288 A1 | | 12/2004 | Ichikawa |
| 2005/0101837 A1 | * | 5/2005 | Kalloo et al. ................. 600/115 |
| 2006/0100614 A1 | | 5/2006 | Long |

FOREIGN PATENT DOCUMENTS

JP    2007-236414    9/2007

OTHER PUBLICATIONS

"Non-Small Cell Lung Cancer V.2.2008", NCCN Clinical Practice Guidelines in Oncology™, National Comprehensive Cancer Network (http://www.nccm.org/professionals/physician_gls/PDF/nscl.pdf).

Kurt G. Tournoy et al., "New American College of Chest Physicians guidelines on mediastinal staging and management of stage IIIA-N2 non-small cell lung cancer: a European perspective", Polskie Archiwum Medycyny Wewnetrznej 2008; 118 (4), P175-P178.

* cited by examiner

*Primary Examiner* — Matthew J Kasztejna
(74) *Attorney, Agent, or Firm* — Scully, Scott, Murphy & Presser, P.C.

(57) ABSTRACT

A treatment instrument for endoscope of the present invention includes a puncture needle having a barb. A lymph node removing method of the present invention includes: an insertion step, wherein an endoscope has an insertable insertion portion which is inserted into an esophagus or a trachea being a lumen inside the body of a subject; the step of inserting a distal end portion arranged at the tip of the insertion portion of the endoscope into the lumen; a confirmation step of confirming the position of a mediastinal lymph node by performing ultrasound scanning using an ultrasound transducer arranged at the distal end portion; an anchoring step of placing an anchoring device which has been inserted through a channel inside the insertion portion of the endoscope, on the mediastinal lymph node by performing the ultrasound scanning; a incision step of cutting a wall of the lumen to make a fistula; and a drawing-in step of drawing the mediastinal lymph node into the lumen with the anchoring device.

16 Claims, 16 Drawing Sheets

LYMPH NODE REMOVING METHOD

CROSS-REFERENCE TO RELATED APPLICATION

This application is a Divisional Application of U.S. application Ser. No. 12/120,831 filed on May 15, 2001, the entire contents of which is incorporated herein by reference.

BACKGROUND OF THE INVENTION

1. Field of the Invention

The present invention relates to a treatment instrument for endoscope and a lymph node removing method, and in particular to a treatment instrument for endoscope suitable for removing a lymph node and a lymph node removing method of removing a lymph node with the use of the treatment instrument for endoscope which protrudes from the distal end portion of an endoscope inserted in an esophagus or a trachea.

2. Description of the Related Art

In a case of lung cancer, diagnosis of non-small cell lung cancer (NSCLC), that is, diagnosis of cancer metastasis to a lymph node is an important prognostic factor. Especially judgment on whether cancer metastasis is recognized on a mediastinal lymph node and a hilum of lung (hereinafter, these are also referred to simply as "lymph nodes") is important in considering operability, preoperative and postoperative treatment, and prognosis.

FIG. 1 is a diagram for illustrating the positions of mediastinal lymph nodes and hilar lymph nodes. As shown in FIG. 1, these lymph nodes are scattered around a trachea 4 and an esophagus 5. In order to check cancer metastasis to each lymph node 2, it is strongly desired to remove and examine a tissue of the lymph node 2.

As a lymph node removing method, a method using a mediastinoscope is performed. In the method using a mediastinoscope, an operator cuts the skin at the bottom of a patient's neck and pushes open the tissue at the front part of the trachea to make a space and insert the mediastinoscope. Then, the operator removes the lymph node 2 around the trachea 4 or the esophagus 5 while looking at an endoscopic image.

SUMMARY OF THE INVENTION

In order to achieve the object, a treatment instrument for endoscope of the present invention includes a puncture needle having a barb.

A lymph node removing method of the present invention includes the following steps: an insertion step, wherein an endoscope has an insertable insertion portion which is inserted into an esophagus or a trachea being a lumen inside the body of a subject; the step of inserting a distal end portion arranged at the tip of the insertion portion of the endoscope into the lumen; a confirmation step of confirming the position of a lymph node by performing ultrasound scanning using an ultrasound transducer arranged at the distal end portion of the endoscope; an anchoring step of placing an anchoring device which has been inserted through a channel inside the insertion portion, on the lymph node by performing the ultrasound scanning; a incision step of cutting a wall of the lumen to make a fistula; and a drawing-in step of drawing the lymph node into the lumen with the anchoring device.

DETAILED DESCRIPTION OF THE PREFERRED EMBODIMENTS

[First Embodiment]

Figure 2:
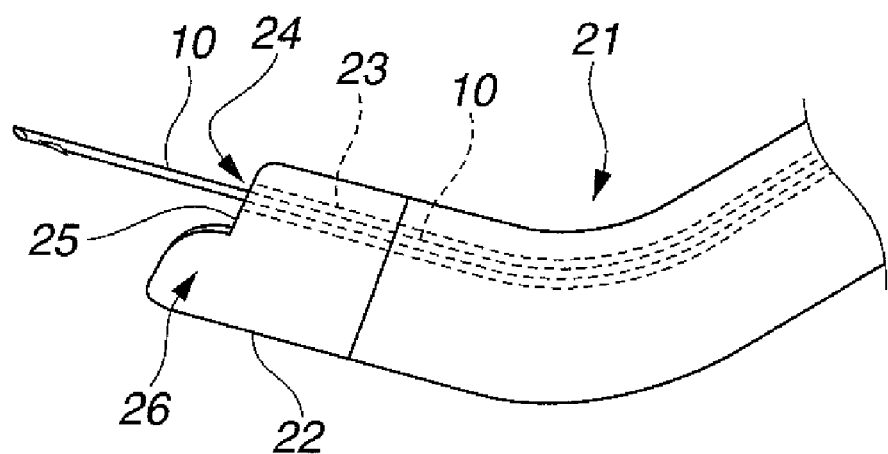
FIG. 2 is a diagram for illustrating the structure of the distal end portion of an endoscope.

A puncture needle 10 which is a treatment instrument for endoscope of a first embodiment of the present invention will be described below with reference to drawings. FIG. 2 is a diagram for illustrating the structure of the distal end portion of an endoscope, and FIG. 3 is a schematic perspective view of the puncture needle, which is the treatment instrument for endoscope of the first embodiment.

As shown in FIG. 2, the treatment instrument for endoscope is a treatment instrument, such as the puncture needle 10, which can be inserted through a channel 23 arranged inside an insertion portion 21 of an endoscope, the insertion portion 21 being insertable into the body of a patient who is a subject, and which can be protruded from a channel outlet 24 of a distal end portion 22 of the insertion portion 21. As shown in FIG. 2, at the distal end portion 22, not only the channel outlet 24 from which the treatment instrument for endoscope, such as the puncture needle 10, protrudes but also optical observation means 25 such as a CCD, an ultrasound transducer 26 for performing ultrasound scanning, and the like are also arranged.

Figure 3:
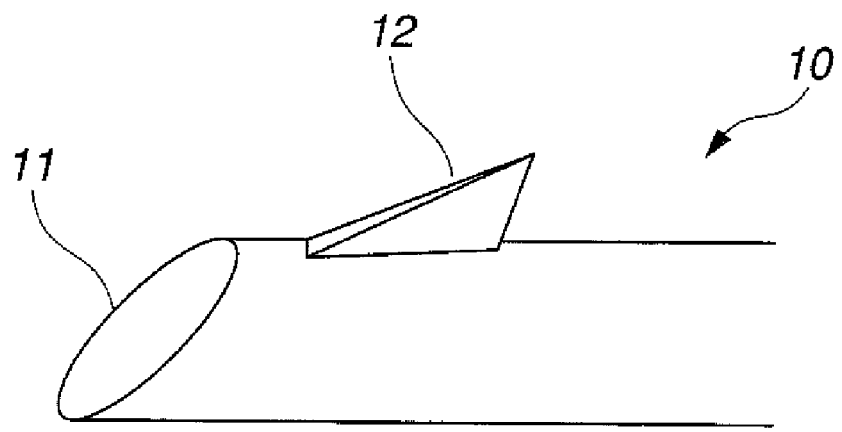
FIG. 3 is a schematic perspective view of a puncture needle, which is a treatment instrument for endoscope of a first embodiment.
Figure 4:
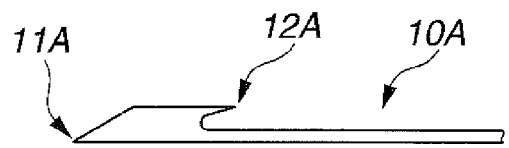
FIG. 4 is a schematic side view for illustrating an example of the puncture needle of the first embodiment.
Figure 5:
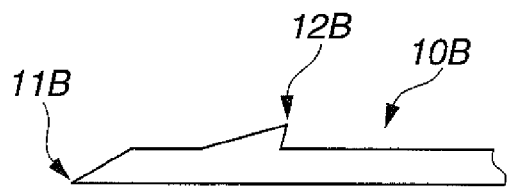
FIG. 5 is a schematic side view for illustrating an example of the puncture needle of the first embodiment.
Figure 6:
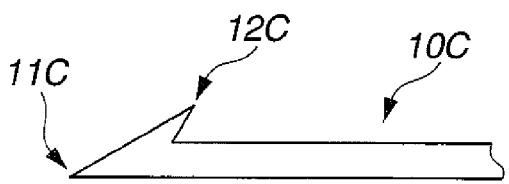
FIG. 6 is a schematic side view for illustrating an example of the puncture needle of the first embodiment.
Figure 7:
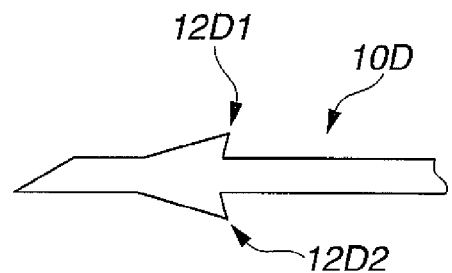
FIG. 7 is a schematic side view for illustrating an example of the puncture needle of the first embodiment.
Figure 8:
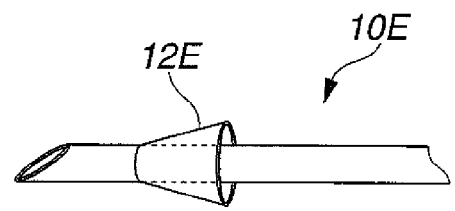
FIG. 8 is a schematic perspective view for illustrating an example of the puncture needle of the first embodiment.
Figure 9:
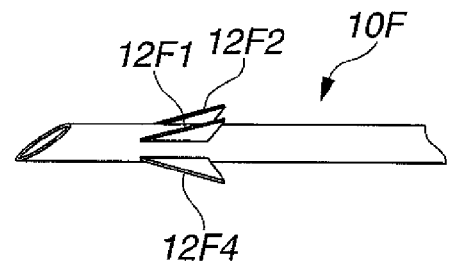
FIG. 9 is a schematic perspective view for illustrating an example of the puncture needle of the first embodiment.

As shown in FIG. 3, the puncture needle 10, which is the treatment instrument for endoscope of the present embodiment, has a barb 12 in a shape sharpened toward the direction opposite to the direction toward which a needle tip 11 is sharpened.

The barb 12 has a so-called anchoring function of preventing the puncture needle 10 being stuck in a target tissue from coming out. In other words, the shape of the barb 12 sharpened in almost the opposite direction is such that prevents the puncture needle 10 being stuck in a target tissue from coming out.

In the case of using the puncture needle 10, which is the treatment instrument for endoscope of the present invention having the anchoring function, an operator can place the puncture needle 10 in a target tissue only by sticking the puncture needle 10 into the target tissue. Therefore, by moving the puncture needle 10 toward the direction of pulling out the puncture needle 10, the operator can certainly draw the target tissue toward him That is, the puncture needle 10 having the barb 12 is an anchoring device for anchoring to a target tissue.

Only by sticking the puncture needle 10, for example, into a lymph node 2, the operator can fix the puncture needle 10 to the lymph node 2. Accordingly, by moving the puncture needle 10 toward the direction of pulling out the puncture needle 10 from the lymph node 2 next, the operator can remove the lymph node 2.

That is, as well as being a treatment instrument with a small diameter which can be easily inserted through the narrow channel 23, the puncture needle 10 is also a treatment instrument for endoscope with good operability, which especially can remove at least a part of a tissue having a certain degree of size like the lymph node 2. Depending on the degree of binding among cells constituting the tissue or the strength of the tissue, the puncture needle 10 can remove the whole tissue.

Especially when the lymph node 2 is not bound to the surrounding region in the body or loosely bound, the operator does not have to cut off the connection part to remove the lymph node 2.

FIGS. 4 to 9 are diagrams for illustrating examples of the puncture needle of the first embodiment. Puncture needles 10A, 10B and 10C shown in FIGS. 4, 5 and 6 have barbs 12A, 12B and 12C, respectively, which are in a shape sharpened toward the direction opposite to the direction toward which needle tips 11A, 11B and 11C are sharpened, respectively. A puncture needle 10D shown in FIG. 7 has multiple barbs 12D1 and 12D2. A puncture needle 10E shown in FIG. 8 has a barb 12E arranged to surround all the circumference. A puncture needle 10F shown in FIG. 9 has multiple barbs 12F1, 12F2 and 12F3 (not shown) and 12F4 arranged to surround the puncture needle 10F. That is, as for the number and the shape of barbs of the puncture needle, various forms are possible if the form is such as to prevent the puncture needle 10 being stuck in a target tissue from coming out.

The tip of a needle may be expressed as a front barb. As already described before, the barb 12 of the puncture needle 10 of the present embodiment performs an operation quite different from that of the front barb which is a needle tip.

[Second Embodiment]

A treatment instrument for endoscope of a second embodiment of the present invention will be described with reference to drawings.

Figure 10:
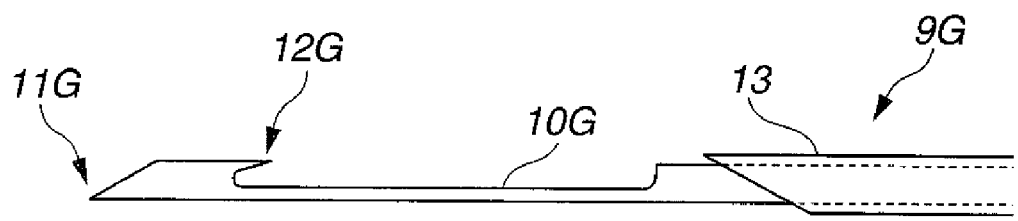
FIG. 10 is a schematic side view for illustrating a treatment instrument for endoscope of a second embodiment.
Figure 11:
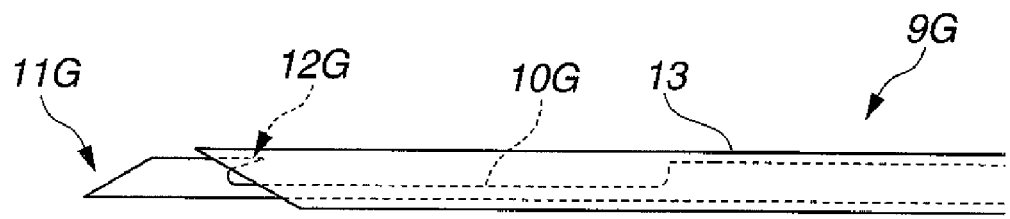
FIG. 11 is a schematic side view for illustrating a treatment instrument for endoscope of the second embodiment.
Figure 12:
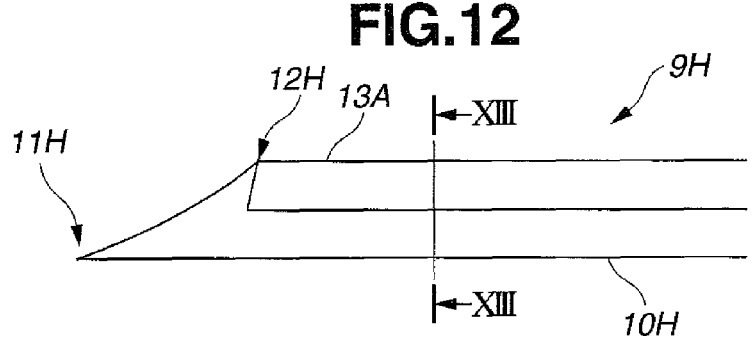
FIG. 12 is a schematic side view for illustrating the treatment instrument for endoscope of the second embodiment.
Figure 13:
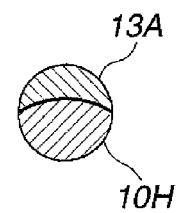
FIG. 13 is a schematic cross-sectional view for illustrating the treatment instrument for endoscope of the second embodiment.

FIGS. 10 and 11 are schematic side views for illustrating the treatment instrument for endoscope of the present embodiment. FIGS. 12 and 13 are schematic cross-sectional views for illustrating the treatment instrument for endoscope of the present embodiment.

The treatment instrument for endoscope of the present embodiment includes a puncture needle having a barb and a barb protecting mechanism for disabling the function of the barb.

A treatment instrument for endoscope 9G shown in FIG. 10 and FIG. 11 includes a puncture needle 10G having a barb 12G and a tube body 13 capable of containing the puncture needle 10G. That is, as shown in FIG. 10, a tube body 13, which is the barb protecting mechanism of the treatment instrument for endoscope 9G, is a barb protecting member provided separately from the puncture needle 10G.

As shown in FIG. 11, the tube body 13 of the treatment instrument for endoscope 9G is a barb protecting member capable of moving on the axis of the puncture needle 10G, which is a so-called barb protecting slider or a barb protecting sheath. Therefore, when the tube body 13 advances up to the side of a needle tip 11G passing the barb 12G of the puncture needle 10G, the tube body 13 covers the barb 12G and disables the function of the barb 12G. By drawing back the puncture needle 10G together with the tube body 13 in this state, the operator can quickly pull out the puncture needle 10G without the barb 12 catching the surrounding tissue.

The treatment instrument for endoscope 9G of the present embodiment makes it possible for the operator to, when having stuck the puncture needle 10G into not a target tissue but a wrong tissue, pull out the puncture needle 10G from the wrong tissue. Furthermore, the treatment instrument for endoscope 9G makes it possible to disable the function of the barb 12G by the tube body 13 when the puncture needle 10G is inserted through the tube body 13, and therefore, there is not a possibility that the channel tube is damaged when the puncture needle 10G is inserted through a channel 23.

Next, a treatment instrument for endoscope which has a barb protecting member to be fitted a puncture needle will be described with the use of FIGS. 12 to 16. FIGS. 12 to 16 are diagrams for illustrating the treatment instrument for endoscope which has a barb protecting member to be fitted with a puncture needle, and FIG. 13 shows the structure of the cross section by the line XIII-XIII in FIG. 12.

Figure 14:
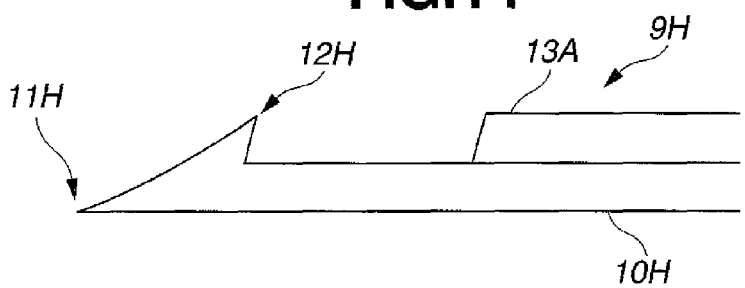
FIG. 14 is a schematic side view for illustrating a treatment instrument for endoscope of the second embodiment.

A treatment instrument for endoscope 9H shown in FIGS. 12 to 14 includes a puncture needle 10H having a barb 12H, and a fitted body 13A which is a barb protecting member. The fitted body 13A, which is a barb protecting member, is fitted with the puncture needle 10H. The fitted body 13A can move parallel on the puncture needle 10H. Therefore, when moving to side of the needle tip 11H of the puncture needle 10H, the fitted body 13A is fitted to the barb 12H and disables the function of the barb 12H, as shown in FIG. 12. On the other hand, when the fitted body 13A moves to the opposite side of the needle tip 11H of the puncture needle 10H, the barb 12H is exposed, and the function of the barb 12H is enabled, as shown in FIG. 14. As shown in FIG. 13, the puncture needle 10H and the fitted body 13A are fitted with each other.

The treatment instrument for endoscope 9H has advantages similar to the treatment instrument for endoscope 9 and the like, and furthermore, it is possible to shorten the diameter of the treatment instrument for endoscope 9H in comparison with the treatment instrument for endoscope 9G having the tube body 13, by using the fitted body 13A as a barb protecting member. The treatment instrument for endoscope 9H is also superior to the treatment instrument for endoscope 9 and the like in cleanability.

Figure 15:
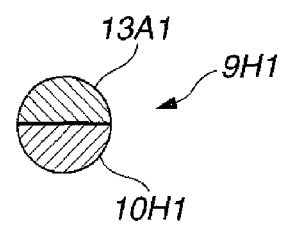
FIG. 15 is a schematic cross-sectional view for illustrating the treatment instrument for endoscope of the second embodiment.

FIG. 15 shows a cross-sectional structure of a part of a treatment instrument for endoscope 9H1 which is similar to the part in FIG. 13, and, in the treatment instrument for endoscope 9H1, a puncture needle 10H1 and a fitted body 13A1, which is a barb protecting member, are in contact with each other via a plane part. By being provided with a binding portion for binding the puncture needle 10H1 and the fitted body 13A1 as appropriate, the treatment instrument for endoscope 9H1 has advantages substantially similar to those in the case where the puncture needle 10H1 and the fitted body 13A1 are fitted with each other. Accordingly, the treatment instrument for endoscope 9H1 is an embodiment of the treatment instrument for endoscope of the present embodiment which has a fitted body as a barb protecting member.

Figure 16:
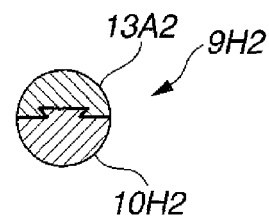
FIG. 16 is a schematic cross-sectional view for illustrating a treatment instrument for endoscope of the second embodiment.

Furthermore, FIG. 16 shows a cross-sectional structure of a treatment instrument for endoscope 9H2 which is similar to the cross-sectional structure in FIG. 13. The treatment instrument for endoscope 9H2 indicates an example of a treatment instrument for endoscope in which a puncture needle 10H2 and a fitted body 13A2, which is a barb protecting member, are firmly fitted with each other.

That is, in the treatment instrument for endoscope of the present embodiment, which has a fitted body as a barb protecting member, various well-known fitting structures can be used as the fitting structure thereof.

Figure 17:
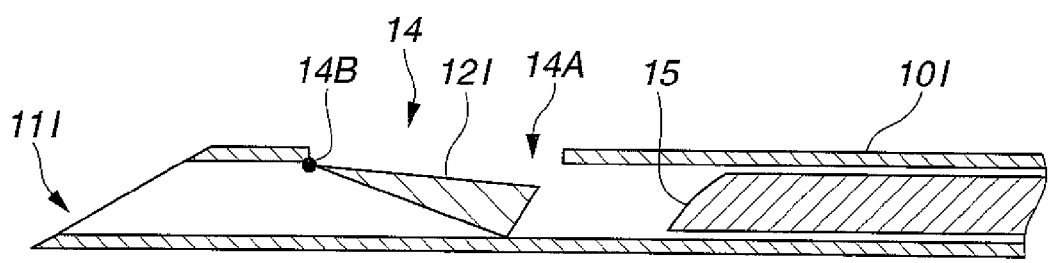
FIG. 17 is a schematic cross-sectional view for illustrating the treatment instrument for endoscope of the second embodiment.
Figure 18:
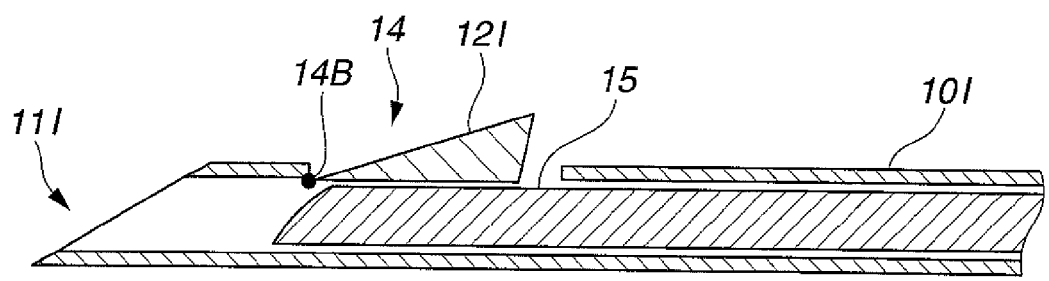
FIG. 18 is a schematic cross-sectional view for illustrating the treatment instrument for endoscope of the second embodiment.

Next, the treatment instrument for endoscope shown in FIGS. 17 and 18 is a puncture needle 10I having a barb 12I. The barb 12I can be contained inside the puncture needle 10I. That is, the barb protecting mechanism of the puncture needle 10I is a barb protecting portion 14 which contains the barb 12I. As shown in FIG. 17, there is a cavity inside the puncture needle 10I, and the barb 12I is contained inside the puncture needle 10I. A slit-shaped opening 14A is arranged on the puncture needle 10I, and the barb 12I is arranged in a manner that it can rotate around a fixed position 14B.

Therefore, by pushing the barb 12I toward the side of the distal end portion 11I by an operation wire 15 or the like which can be inserted inside the puncture needle 10I, the operator can cause the puncture needle 10I to protrude from the opening 14A to be on the circumferential surface, as shown in FIG. 18. The operator can cause the barb 12I protruding from the circumferential surface of the puncture needle 10I to be contained inside the puncture needle 10I again by an operation of drawing back the operation wire 15.

Since having the barb protecting portion 14, which is a barb protecting mechanism for disabling the function of the barb 12I, the puncture needle 10I can have operations and advantages similar to the treatment instrument for endoscope 9G. It is also possible to shorten the diameter of the puncture needle 10I in comparison with the treatment instrument for endoscope 9G.

The structure of the barb protecting portion in which the barb is contained inside the puncture needle is not limited to the case of the puncture needle 10I. Various methods such as a driving system utilizing air pressure are possible. Though the puncture needle 10I has a structure in which the barb 12I can be freely taken out and put in through the opening 14A of the puncture needle 10I, such a structure is also possible in which, after a barb contained inside the puncture needle 10I once having protruded outside the puncture needle 10I, the barb cannot be contained again.

Description has been made on the treatment instrument for endoscope which includes a puncture needle, a puncture needle and a tube body, or a puncture needle and a fitted body. The treatment instrument for endoscope is not limited to a single treatment instrument. Any treatment instrument for endoscope is possible if it can be inserted through the channel 23 and can project from a distal end portion 22 of an insertion portion 21. For example, a sheath having multiple lumens inside, and a sheath including multiple treatment instruments inserted in lumens can be given as examples of the treatment instrument for endoscope of the present embodiment. For example, a sheath which includes a treatment instrument having a cutting function, in addition to a puncture needle and a tube body, can be also preferably used as one treatment instrument for endoscope of the present embodiment as a whole. In the case of using a ring-shaped high-frequency snare, that is, a high-frequency snare having a variable-sized ring at the distal end portion as a treatment instrument having a cutting function, it is preferable that a puncture needle, which is an anchoring device, is arranged in the ring of the high-frequency snare. Furthermore, a sheath which is provided with a high-frequency output portion capable of performing electrification as a treatment instrument having a cutting function, on the circumference part thereof can be also preferably used as the treatment instrument for endoscope of the present embodiment.

A so-called guide wire which is provided with a puncture needle having a barb at the distal end portion of the wire can be also preferably used as the treatment instrument for endoscope of the present embodiment.

Furthermore, it is preferable that at least a part of the treatment instrument for endoscope of the present embodiment has a reflection processed part which can be recognized by ultrasound observation. The reflection processed part is formed, for example, by forming an ultrasound reflecting surface which has been ring-shaped-dimple processed. The ring-shaped ultrasound reflecting surface is configured by a relatively deep circular concave portion and a circular convex portion lower than the surface which is arranged at the center of the circular concave portion. By reflecting an ultrasound signal from an ultrasound transducer 26 by the reflection processed part, a lot of reflected ultrasound signals can be inputted to the ultrasound transducer 26, and recognition in ultrasound observation is facilitated.

Alternatively, a surface provided with a lot of grooves having a V-shaped cross section, a surface obtained by processing a rough surface with sand abrasive or the like so that an ultrasound wave can be easily reflected, or the like can be used as the reflection processed part. Furthermore, the reflection processed part can be formed by enclosing a substance with an acoustic impedance different from that of a living body, for example, air bubbles. The reflection processed part can be recognized by ultrasound observation more easily than parts other than the reflection processed part.

In the case of a puncture needle having a barb protecting mechanism, the barb protecting mechanism can be used to pull out, from a tissue into which the puncture needle having a barb is anchored, the puncture needle. For example, in the case of the puncture needle 10G shown in FIG. 10, the effect of the barb 12G can be disabled by moving the tube body 13 forward as shown in FIG. 11, and thereby, the puncture needle 10G can be pulled out.

In the case of a puncture needle without the barb protecting mechanism, the puncture needle being stuck in a tissue is stuck deeper into the tissue so that the distal end portion of the needle, including the barb, is pushed out of the tissue. Then, by cutting the puncture needle at an appropriate position, the puncture needle 10G can be removed from the tissue.

[Third Embodiment]

Description will be made below on a treatment instrument for endoscope and a lymph node removing method according to a third embodiment of the present invention, with reference to drawings.

Figure 1:
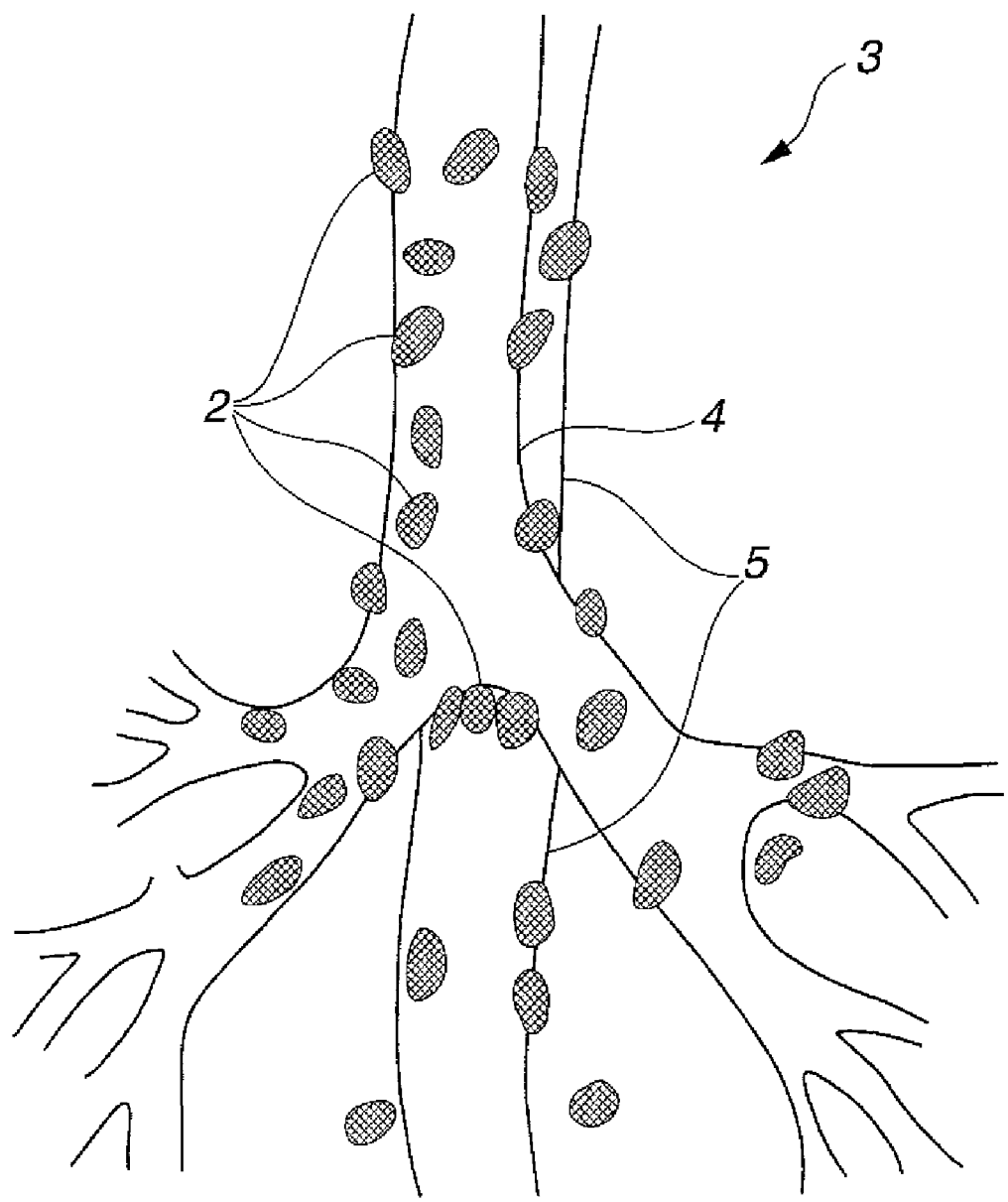
FIG. 1 is a diagram for illustrating the positions of mediastinal lymph nodes and hilar lymph nodes.
Figure 19:
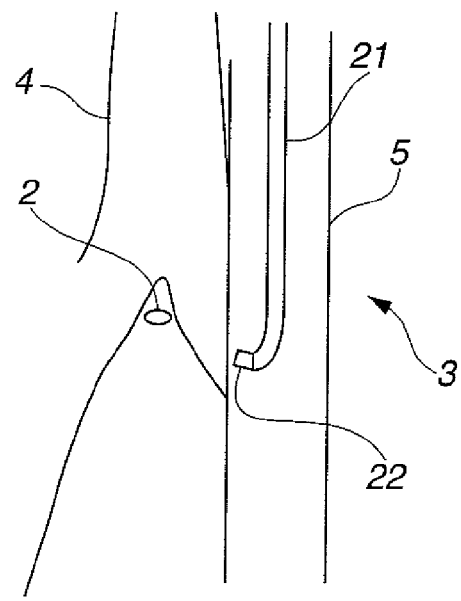
FIG. 19 is a diagram for illustrating a lymph node removing method of a third embodiment.
Figure 20:
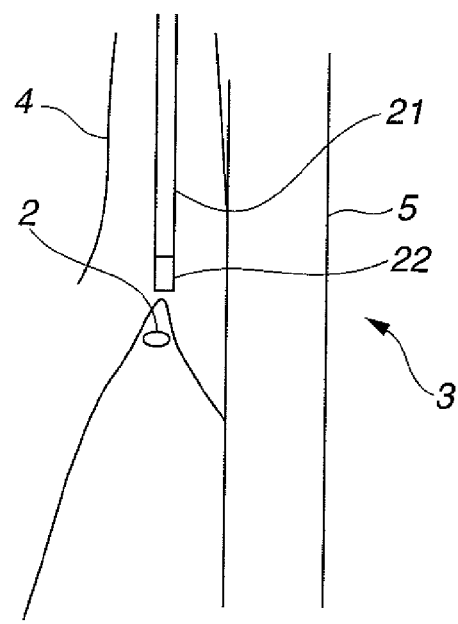
FIG. 20 is a diagram for illustrating a lymph node removing method of the third embodiment.

FIGS. 19 and 20 are diagrams for illustrating the lymph node removing method of the present embodiment. As described before with the use of FIG. 1, lymph nodes 2 exist around a trachea 4 or an esophagus 5. Therefore, by inserting a distal end portion 22 arranged at the tip of an insertion portion 21 of an endoscope into the trachea 4 or the esophagus 5, causing the treatment instrument for endoscope to protrude from the distal end portion 22 and performing treatment, an operator can remove a lymph node 2. FIGS. 19 and 20 show the endoscope seen from diagonally backward of the body of a patient, in the case of insertion via esophagus in which insertion is performed by way of the esophagus 5 and in the case of insertion via trachea in which insertion is performed by way of the trachea 4, respectively.

Figure 21:
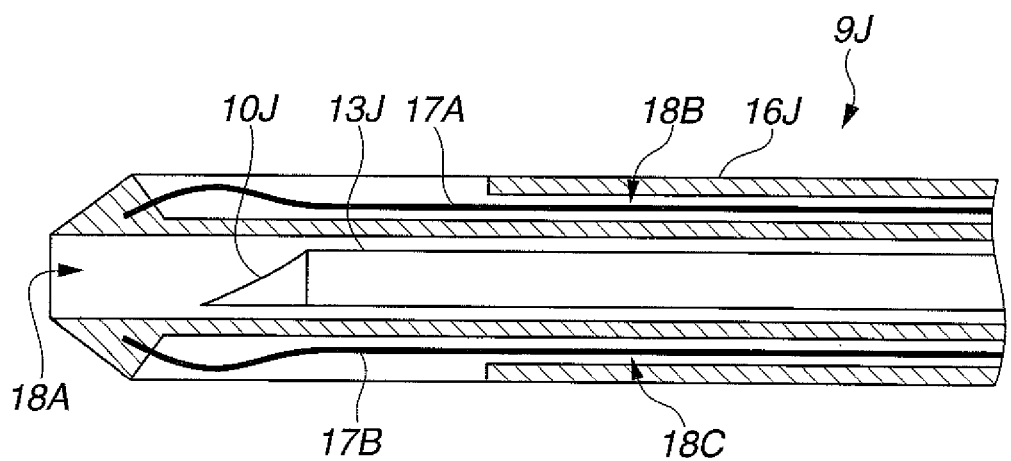
FIG. 21 is a schematic cross-sectional view for illustrating a treatment instrument for endoscope of the third embodiment.
Figure 22:
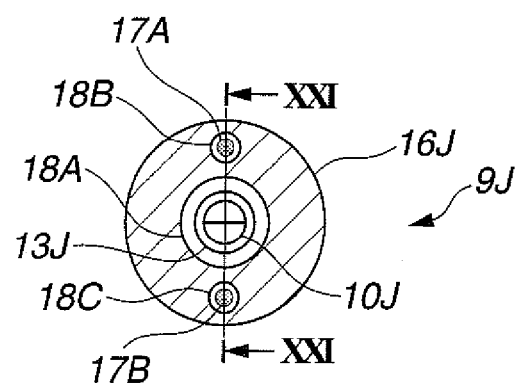
FIG. 22 is a schematic cross-sectional view for illustrating the treatment instrument for endoscope of the third embodiment.

The lymph node removing method of the present embodiment will be described below using the case of insertion via esophagus as an example. In the lymph node removing method of the present embodiment, an anchoring device having the same barb as that of the puncture needle 10 of the first embodiment is used. FIGS. 21 and 22 are schematic cross-sectional views for illustrating a treatment instrument for endoscope 9J of the present embodiment. FIG. 21 shows the cross section by the line XXI-XXI in FIG. 22.

As shown in FIGS. 21 and 22, the treatment instrument for endoscope 9J of the present embodiment includes a sheath 16J having three lumens 18A, 18B and 18C; and a tube body 13J and a puncture needle 10J, and two high-frequency output portions 17A and 17B capable of performing electrification, on the circumference part of the sheath 16J, which are inserted through the lumens 18A, 18B and 18C, respectively. The puncture needle 10J can go forward and backward along the sheath 16J, and the cross section on the rear side of the puncture needle 10J is half-moon shaped. Each of the high-frequency output portions 17A and 17B is an electrode configured by flexible wire. Though the tip thereof is fixed to the sheath 16J, the rear side thereof can go forward and backward along the sheath 16J. On the distal end portion side of each of the lumens 18B and 18C, the circumference part is open so that a slit is formed.

As described above, the treatment instrument for endoscope 9J of the present embodiment includes the puncture needle 10J having a barb, the sheath 16J which disables the operation of the barb, and the sheath 16J where the puncture needle 10J and the sheath 16J can be put into and taken out of. The sheath 16J is provided with the high-frequency output portions 17A and 17B capable of performing electrification, which are members having a cutting function, on the circumference part of the sheath 16J. The high-frequency output portions 17A and 17B can be taken into or taken out of the sheath 16J.

The puncture needle and the like used in the present embodiment are not limited to those described above. Those described in the first or second embodiment can be used as appropriate.

Figure 23:
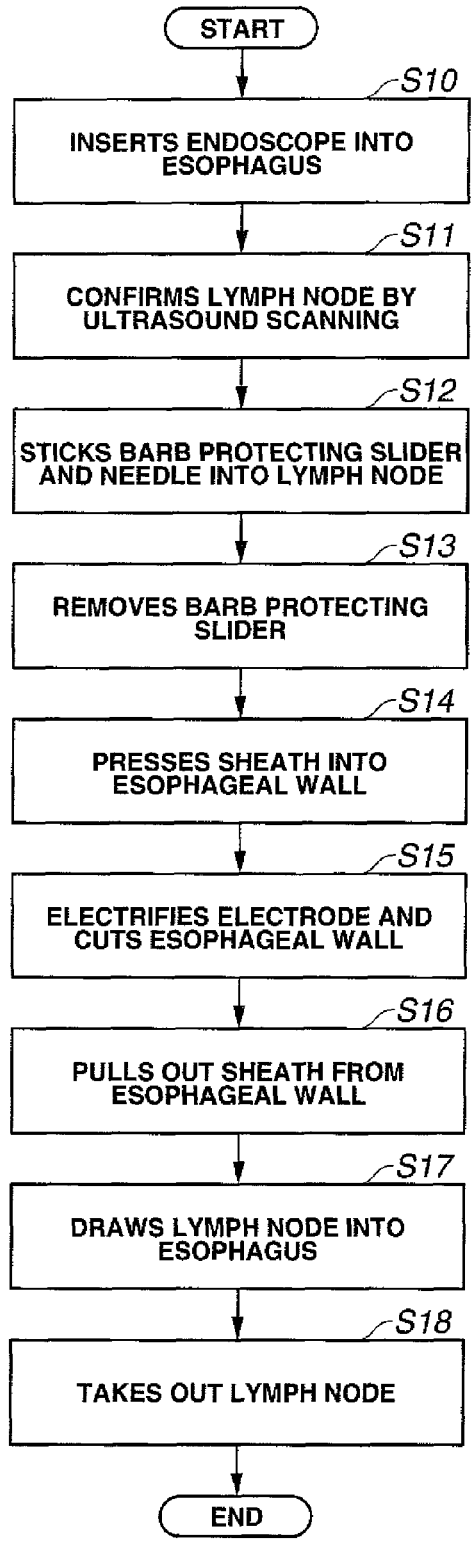
FIG. 23 is a flowchart for illustrating the lymph node removing method of the third embodiment.

FIG. 23 is a flowchart for illustrating the flow of the lymph node removing method of the present embodiment, and FIGS. 24 to 29 are diagrams showing a schematic cross section for illustrating the lymph node removing method of the present embodiment. The flow of the lymph node removing method will be described below in accordance with the flowchart in FIG. 23.

<Step S10> Insertion Step

As shown in FIG. 19, an operator inserts the distal end portion 22 of the insertion portion 21 of the endoscope into the esophagus 5, the insertion portion 21 being insertable into the esophagus 5 of a patient.

<Step S11> Confirmation Step

Similarly to the endoscope shown in FIG. 2, optical observation means 25, an ultrasound transducer 26 for performing ultrasound scanning, and the like are arranged at the distal end portion 22 of the endoscope used in the lymph node removing method of the present embodiment.

Therefore, by performing ultrasound scanning using the ultrasound transducer 26 arranged at the distal end portion 22, the operator can confirm the position of a target lymph node 2. Then, after inserting the distal end portion 22 to the vicinity of the target lymph node 2, the operator inserts the sheath 16J, which is a treatment instrument for endoscope, from a channel port of the endoscope, causes the sheath 16J to go through the channel 23 inside the insertion portion 21 and protrude from the channel outlet 24 at the distal end portion 22 of the endoscope.

<Step S12> Anchoring Step 1

Figure 24:
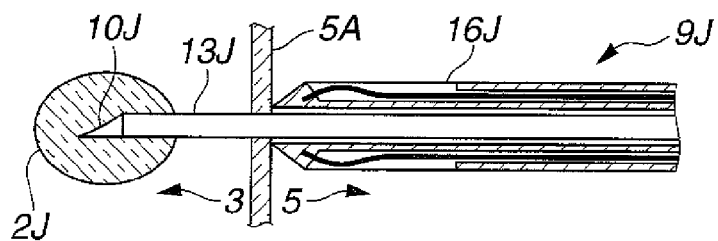
FIG. 24 is a diagram showing a schematic cross section for illustrating the lymph node removing method of the third embodiment.

As shown in FIG. 24, the operator causes the puncture needle 10J, the barb 12J of which is covered with the tube body 13J, to protrude from the sheath 16J, and sticks the puncture needle 10J into the target lymph node 2J existing in a mediastinum 3 from the esophagus 5 via an esophageal wall 5A. Since the function of the barb 12J of the puncture needle 10J has been disabled by the tube body 13J, which is a barb protecting mechanism, the operator can stick the puncture needle 10J again. The operator can also cause the puncture needle 10J to go forward or backward so that the needle tip is appropriately positioned, as necessary.

<Step S13> Anchoring Step 2

Figure 25:
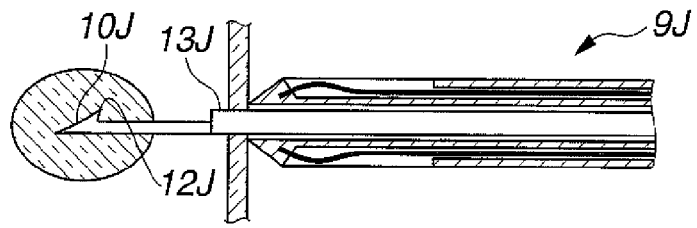
FIG. 25 is a diagram showing a schematic cross section for illustrating the lymph node removing method of the third embodiment.

If the operator can confirm that the puncture needle 10J has been stuck at a correct position by ultrasound observation, he draws back only the tube body 13J, which is a barb protecting mechanism, to himself, in other words, to its proximal end side as shown in FIG. 25.

Then, the barb 12J which has been covered with the tube body 13J is exposed within the lymph node 2J, and thereby, the puncture needle 10J is placed in the lymph node 2J, in other words, it is anchored.

<Step S14>

Figure 26:
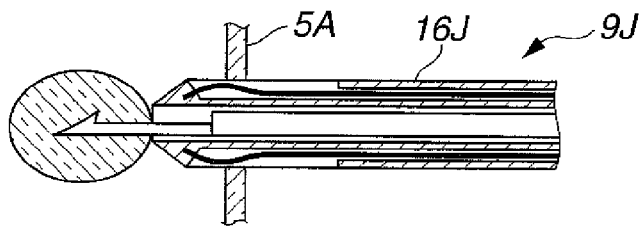
FIG. 26 is a diagram showing a schematic cross section for illustrating the lymph node removing method of the third embodiment.

As shown in FIG. 26, the operator presses the sheath 16J into the esophageal wall 5A and causes the sheath 16J to cut into the esophageal wall 5A. The tip of the sheath 16J shown in FIG. 26 is in a tapered shape. However, it is also possible to form grooves like drill grooves at the tip of the sheath so that the sheath can rotatingly cut into the esophageal wall 5A.

<Step S15> Incision Step

Figure 27:
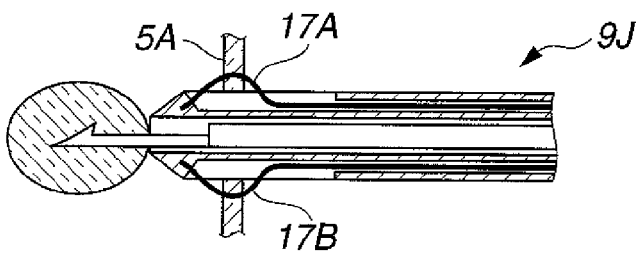
FIG. 27 is a diagram showing a schematic cross section for illustrating the lymph node removing method of the third embodiment.

As shown in FIG. 27, the operator draws out the two high-frequency output portions 17A and 17B from the opening portions of the lumens 18B and 18C so that the high-frequency output portions 17A and 17B are in contact with the esophageal wall 5A.

Then, by applying a high-frequency current to the two high-frequency output portions 17A and 17B, the operator cuts the esophageal wall 5A. After the cut processing, the high-frequency output portions 17A and 17B are contained in the lumens 18B and 18C.

<Step S16>

Figure 28:
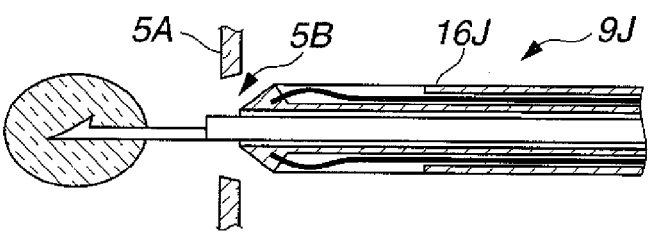
FIG. 28 is a diagram showing a schematic cross section for illustrating the lymph node removing method of the third embodiment.

As shown in FIG. 28, when the operator pulls out the sheath 16J from the esophageal wall 5A, a fistula 5B is formed in the esophageal wall 5A.

<Step S17> Drawing-in Step

Figure 29:
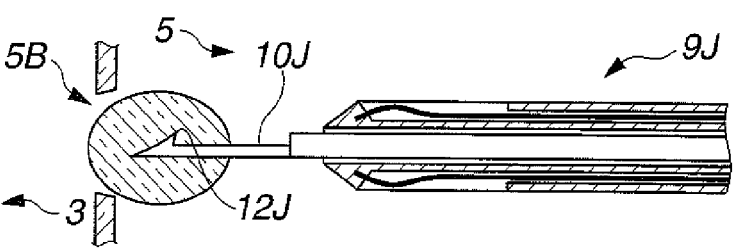
FIG. 29 is a diagram showing a schematic cross section for illustrating the lymph node removing method of the third embodiment.

As shown in FIG. 29, only by drawing back the puncture needle 10J anchored in the lymph node 2J by the barb 12J or the sheath 16J, the operator can draw the lymph node 2J out of the mediastinum 3 into the esophagus 5 via the fistula 5B.

<Step S18> Taking-out Step

By performing an operation of drawing out the insertion portion 21 to the outside of the patient's body, or the like, the operator can take out the lymph node 2J to the outside of the body.

In the lymph node removing method of the present embodiment, the taking-out step is not an indispensable step. That is, it is also possible for the operator to examine the lymph node 2J taken into the esophagus 5 in the esophagus 5 with the use of an examination endoscope, a treatment instrument for examination endoscope, or the like.

As described above, the lymph node removing method of the present embodiment using the treatment instrument for endoscope 9J is a low-invasiveness method, and, it is possible to draw out almost the whole target lymph node 2 by the method. Furthermore, since the lymph node removing method of the present embodiment using the treatment instrument for endoscope 9J can be performed with one treatment instrument for endoscope, the treatment time can be shortened, and thus, an operator's fatigue or waste of a patient's physical strength can be reduced.

[Fourth Embodiment]

Next, description will be made on a treatment instrument for endoscope and a lymph node removing method according to a fourth embodiment of the present invention, with reference to drawings. Since the lymph node removing method and the like of the present embodiment are similar to the lymph node removing method of the third embodiment and the like, description of the same steps will be omitted.

Figure 30:
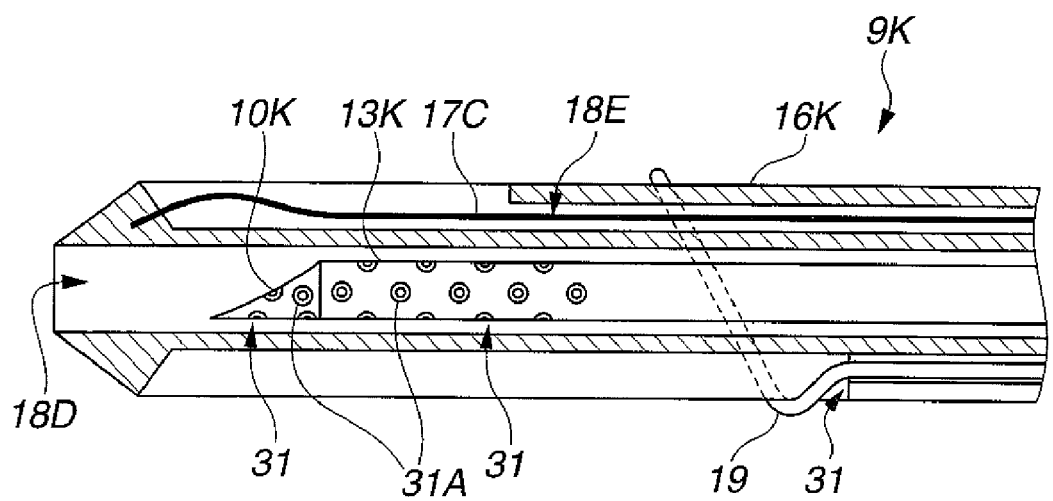
FIG. 30 is a schematic cross-sectional view for illustrating a treatment instrument for endoscope of a fourth embodiment.
Figure 31:
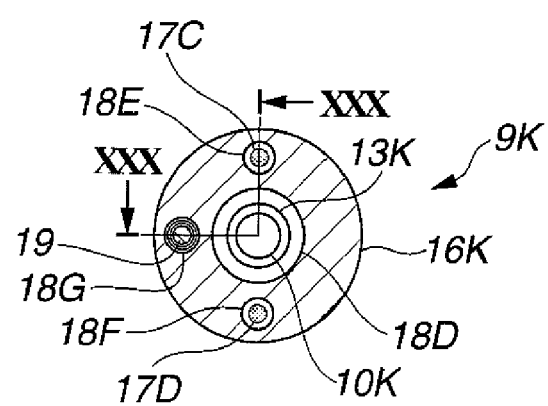
FIG. 31 is a schematic cross-sectional view for illustrating the treatment instrument for endoscope of the fourth embodiment.

FIGS. 30 and 31 are schematic cross-sectional views for illustrating a treatment instrument for endoscope 9K of the present embodiment, and FIG. 30 shows the cross section by the line XXX-XXX in FIG. 31.

As shown in FIGS. 30 and 31, the treatment instrument for endoscope 9K of the present embodiment is configured by a sheath 16K having four lumens 18D, 18E, 18F and 18G inside; and a tube body 13K and a puncture needle 10K having a barb, two high-frequency output portions 17C and 17D capable of performing electrification, on its circumference part, and a high-frequency snare 19 having a ring-shaped portion, which are inserted through the lumens 18D, 18E, 18F and 18G, respectively. The high-frequency snare 19 is contained in a snare sheath (not shown), and each of the high-frequency snare 19 and the snare sheath can go forward and backward along the sheath 16K.

At least a part of the tube body 13K and the puncture needle 10K of the treatment instrument for endoscope 9K is a dimple portion, which is a ultrasound reflection part 31 recognized by ultrasound observation. Multiple dimples 31A are formed on the ultrasound reflection part 31, so that recognition is easily performed in ultrasound observation. It is also possible to, by forming different kinds of reflection processed parts on the tube body 13K and the puncture needle 10K, make it easier to identify both of them by ultrasound observation.

As shown in FIG. 30, the ring of the high-frequency snare 19 is arranged so as to surround the sheath 16K. That is, the puncture needle 10K is arranged within the ring of the high-frequency snare 19.

As described above, the treatment instrument for endoscope 9K of the present embodiment includes the puncture needle 10K having a barb, the tube body 13K which disables the operation of the barb, and the sheath 16K where the puncture needle 10K can be put into and taken out of. The ring-shaped high-frequency snare 19 having a cutting function and the high-frequency output portions 17C and 17D can be put into and taken out of the sheath 16K. The puncture needle 10K is arranged within the ring of the high-frequency snare 19. A part of the tube body 13K and the puncture needle 10K, which is at least a part of the treatment instrument for endoscope 9K, has the reflection part 31 which is recognized by ultrasound observation.

Figure 32:
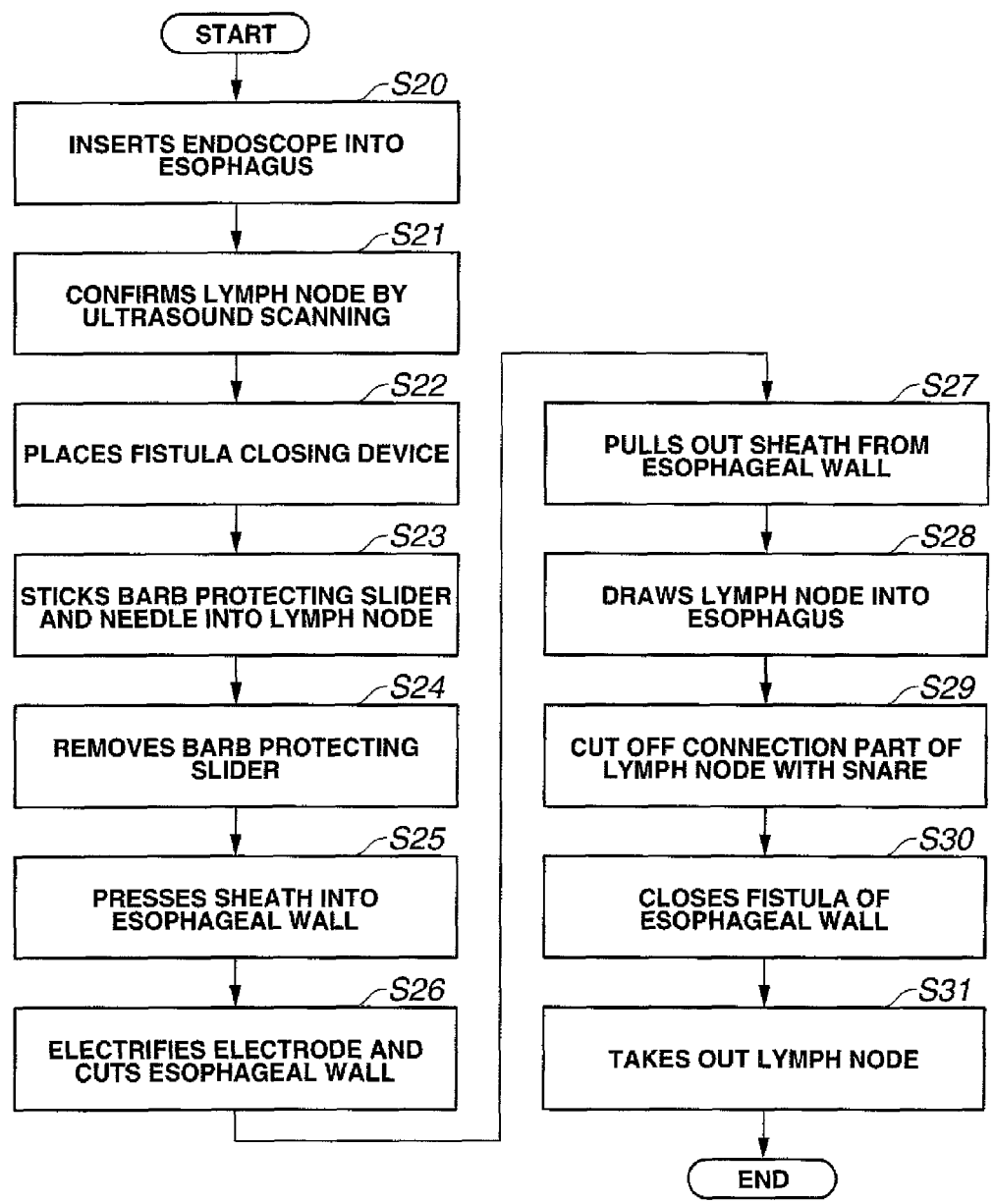
FIG. 32 is a flowchart for illustrating the flow of a lymph node removing method of the fourth embodiment.

FIG. 32 is a flowchart for illustrating the flow of the lymph node removing method of the present embodiment, and FIGS. 33 to 38 are schematic cross-sectional views for illustrating the lymph node removing method of the present embodiment. The flow of the lymph node removing method of the present embodiment will be described below in accordance with the flowchart in FIG. 32.

<Step S20> Insertion Step

This step is almost the same as the step of the lymph node removing method of the third embodiment.

<Step S21> Confirmation Step

This step is almost the same as the step of the lymph node removing method of the third embodiment.

\<Step S22\> Fistula Closing Device Placing Step

The lymph node removing method of the present embodiment has a fistula closing step of closing the fistula of the esophageal wall made by the incision step after drawing out the lymph node into the esophagus. Furthermore, the lymph node removing method has a fistula closing device placing step of placing a fistula closing device on the esophageal wall to be used at the fistula closing step.

It is preferable to use a device called T-bar, which is disclosed in U.S. Pat. No. 4,235,238 and U.S. patent application Ser. No. 11/863,899 as the fistula closing device. The T-bar is configured by bars, that is, rods, a string member and a stopper.

Figure 33:
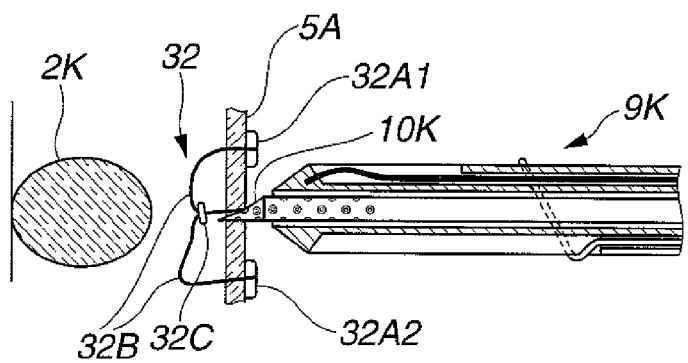
FIG. 33 is a schematic cross-sectional view for illustrating the lymph node removing method of the fourth embodiment.

FIG. 33 shows that a T-bar 32 configured by two bars 32A1 and 32A2, a string member 32B and a stopper 32C is placed on an esophageal wall 5A with the use of the puncture needle 10K. That is, the T-bar 32 can be contained inside the puncture needle 10K having a cavity portion, and the T-bar 32 is placed on the esophageal wall 5A with the use of the puncture needle 10K. An operator determines the position to place the T-bar 32 in consideration of the position on the esophageal wall 5A to be cut.

Figure 34:
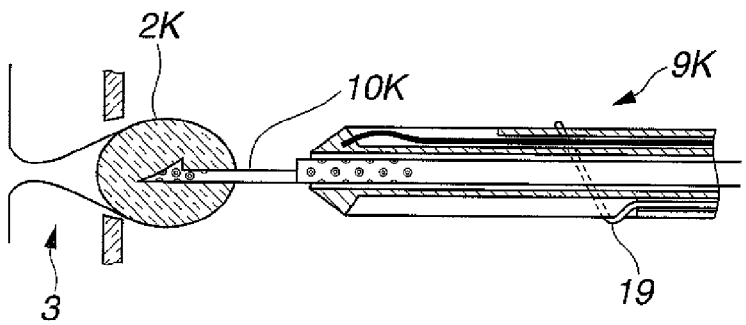
FIG. 34 is a schematic cross-sectional view for illustrating the lymph node removing method of the fourth embodiment.
Figure 35:
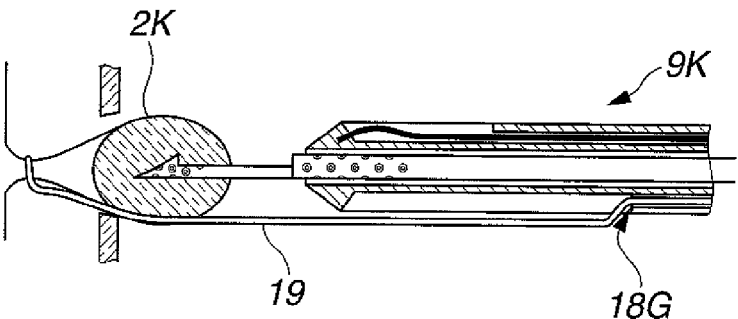
FIG. 35 is a schematic cross-sectional view for illustrating the lymph node removing method of the fourth embodiment.
Figure 36:
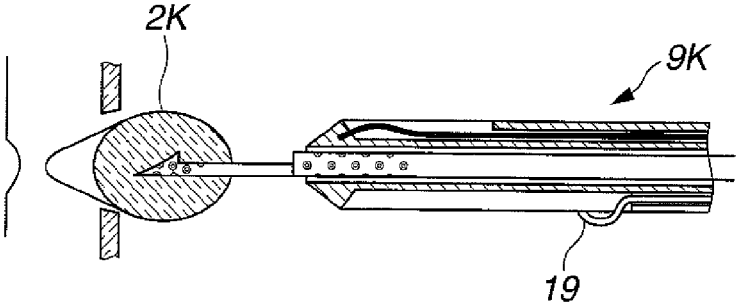
FIG. 36 is a schematic cross-sectional view for illustrating the lymph node removing method of the fourth embodiment.

The T-bar 32 is not shown in FIGS. 34 to 36.

The fistula closing device is not limited to the T-bar 32 configured by two bars, and well-known T-bars with various structures can be used.

\<Step S23\> Anchoring Step 1

This step is almost the same as the step of the lymph node removing method of the third embodiment.

\<Step S24\> Anchoring Step 2

This step is almost the same as the step of the lymph node removing method of the third embodiment.

\<Step S25\>

This step is almost the same as the step of the lymph node removing method of the third embodiment.

\<Step S26\> Incision Step

This step is almost the same as the step of the lymph node removing method of the third embodiment.

\<Step S27\>

This step is almost the same as the step of the lymph node removing method of the third embodiment.

\<Step S28\> Drawing-in Step

This step is almost the same as the step of the lymph node removing method of the third embodiment. However, as shown in FIG. 34, a lymph node 2K is connected with a different tissue of the mediastinum 3. Therefore, the operator cannot remove the lymph node 2K even if he draws back the puncture needle 10K anchored in the lymph node 2K.

\<Step S29\> Separation Step

As shown in FIG. 35, the operator causes the high-frequency snare 19 to protrude from the lumen 18G and puts the ring of the high-frequency snare 19 around the vicinity of the root of the lymph node 2K. Then, by applying a high-frequency current to the high-frequency snare 19, the operator cut off the connection part between the lymph node 2K and the surrounding tissue to separate the lymph node 2K from the surrounding tissue as shown in FIG. 36.

\<Step S30\> Fistula Closing Step

Figure 37:
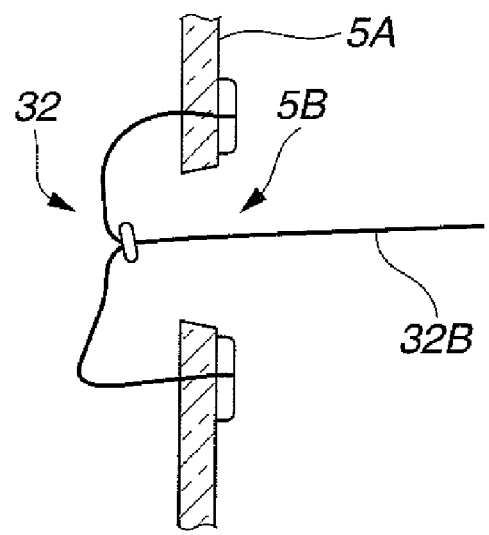
FIG. 37 is a schematic cross-sectional view for illustrating the lymph node removing method of the fourth embodiment.

FIG. 37 shows the state of the fistula 5B on the esophageal wall 5A and the T-bar 32 placed at the fistula closing device placing step after the lymph node 2K is removed.

Figure 38:
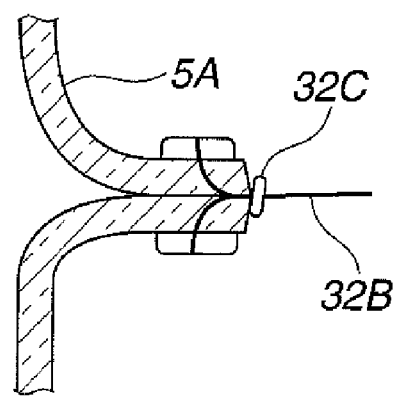
FIG. 38 is a schematic cross-sectional view for illustrating the lymph node removing method of the fourth embodiment.

In the lymph node removing method of the present embodiment, the operator can close the fistula 5B on the esophageal wall 5A with the stopper 32C by pulling the string member 32B of the T-bar 32, as shown in FIG. 38. Even if the fistula 5B closed with the use of the T-bar 32 is not completely closed, it is substantially not a problem. At the stage where the fistula 5B is completely closed by the recovery function of the living body, the bars 32A1 and 32A2 and the stopper 32C come off from the wall of the esophagus 5 and discharged from the body.

\<Step S31\> Taking-out Step

This step is almost the same as the step of the lymph node removing method of the third embodiment. Similarly to the lymph node removing method of the third embodiment, the taking-out step is not an indispensable step in the lymph node removing method of the present embodiment.

As described above, in the treatment instrument for endoscope 9K of the present embodiment and the lymph node removing method of the present embodiment, operation effects similar to those of the treatment instrument for endoscope 9 and the like, and the lymph node removing method of the third embodiment can be obtained. Furthermore, the operator can take out even the lymph node 2K which is connected with a different tissue of the mediastinum 3. Furthermore, in the lymph node removing method of the present embodiment, by using the treatment instrument for endoscope 9K having the high-frequency snare 19, it is possible not only to perform an operation even in the case where the endoscope has only one channel but also to shorten the operation time.

Furthermore, in the lymph node removing method of the present embodiment, it is possible to close the fistula 5B by the fistula closing device. Therefore, according to the lymph node removing method of the present embodiment, a patient recovers sooner.

[Fifth Embodiment]

A treatment instrument for endoscope and a lymph node removing method according to a fifth embodiment of the present invention will be described below with reference to drawings. Since the lymph node removing method of the present embodiment is similar to the lymph node removing method of the third embodiment, description of the same steps will be omitted.

In the lymph node removing method of the present embodiment, an operator removes a target lymph node 2L while observing an endoscopic image picked up by optical observation means 25 arranged at a distal end portion 22 inserted in a mediastinum 3.

Figure 39:
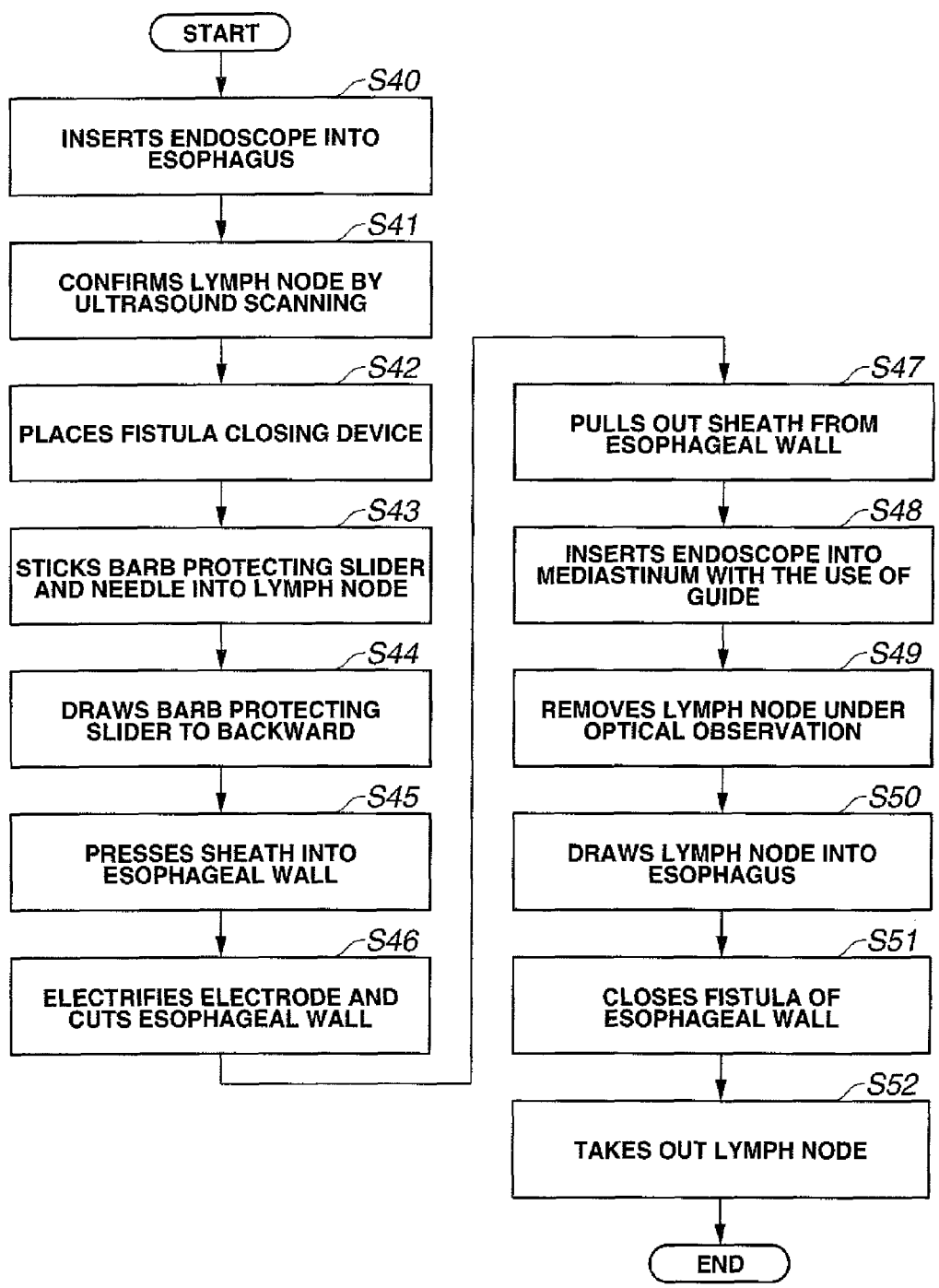
FIG. 39 is a flowchart for illustrating the flow of a lymph node removing method of a fifth embodiment.
Figure 40:
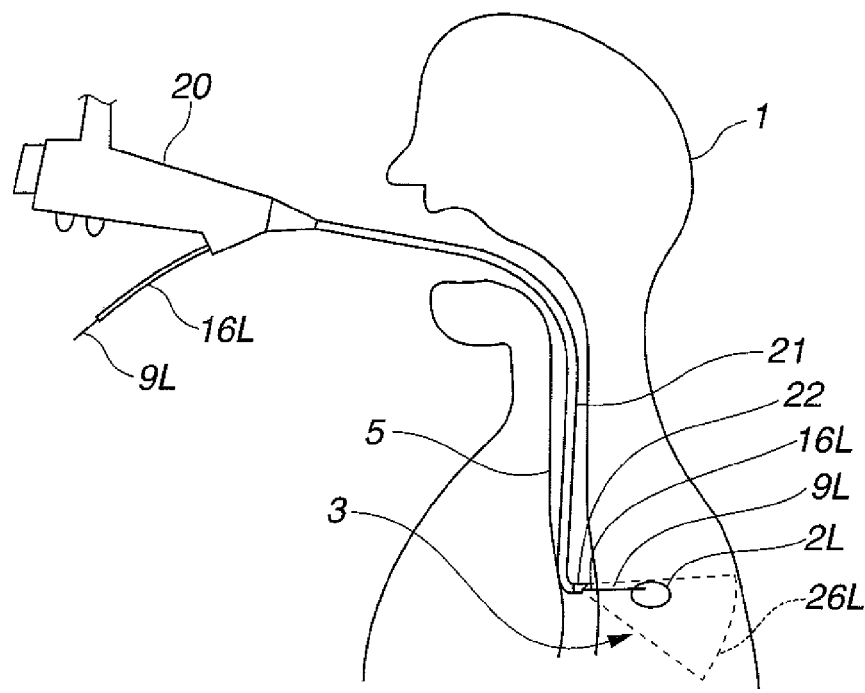
FIG. 40 is a diagram for illustrating the lymph node removing method of the fifth embodiment.
Figure 41:
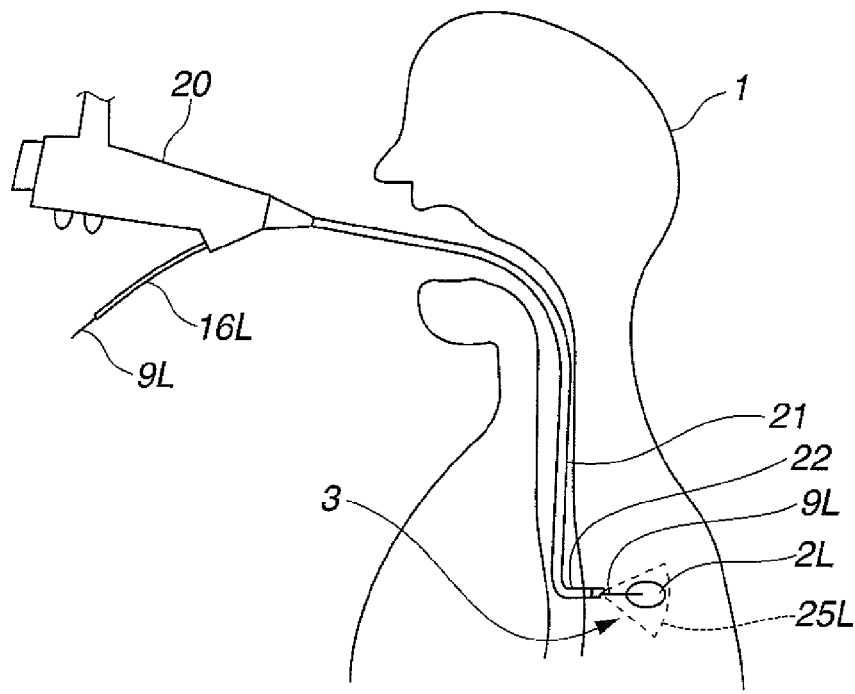
FIG. 41 is a diagram for illustrating the lymph node removing method of the fifth embodiment.

FIG. 39 is a flowchart for illustrating the flow of the lymph node removing method of the present embodiment, and FIGS. 40 and 41 are diagrams for illustrating the lymph node removing method of the present embodiment. The flow of the lymph node removing method will be described below in accordance with the flowchart in FIG. 39.

\<Step S40\> Insertion Step

This step is almost the same as the step of the lymph node removing method of the third embodiment.

\<Step S41\> Confirmation Step

This step is almost the same as the step of the lymph node removing method of the third embodiment.

\<Step S42\> Fistula Closing Device Placing Step

This step is almost the same as the step of the lymph node removing method of the fourth embodiment.

\<Step S43\> Anchoring Step 1

This step is almost the same as the step of the lymph node removing method of the third embodiment. In the lymph node removing method of the present embodiment, however, a sheath through which a guide wire can be inserted is used as a treatment instrument for endoscope. As shown in FIG. 40, after inserting the distal end portion 22 of an insertion portion 21 of an endoscope 20 into an esophagus 5 of a patient 1, who is a subject, the operator inserts a sheath 16L into the channel from the forceps insertion hole of the endoscope 20.

A guide wire 9L is inserted in a lumen inside the sheath 16L, and the guide wire 9L protrudes from the distal end portion 22 via the sheath 16L. The operator sticks a puncture needle which having a barb which is arranged at the distal end portion of the guide wire 9L, into the target lymph node 2L in the mediastinum 3 via an esophageal wall 5A of the esophagus 5. In the present embodiment, the guide wire 9L is an anchoring device which is a treatment instrument for endoscope.

The operator can confirm the position of the target lymph node 2L existing within an ultrasound scanning range 26L by ultrasound scanning using the ultrasound transducer 26 arranged at the distal end portion 22.

<Step S44> Anchoring step 2

This step is almost the same as the step of the lymph node removing method of the third embodiment.

<Step S45>

This step is almost the same as the step of the lymph node removing method of the third embodiment.

<Step S46> Incision Step

This step is almost the same as the step of the lymph node removing method of the third embodiment.

<Step S47>

This step is almost the same as the step of the lymph node removing method of the third embodiment.

<Step S48> Insertion-into-mediastinum Step

As shown in FIG. 41, the operator inserts the distal end portion 22 of the endoscope into the mediastinum 3 using the guide wire 9L as a guide. Since the puncture needle at the tip of the guide wire 9L is anchored in the target lymph node 2L, the guide wire 9L does not come out from the lymph node 2L even if it is pulled. Therefore, the operator can easily insert the distal end portion 22 up to the vicinity of the lymph node 2L, that is, up to an appropriate position in the mediastinum 3 where the lymph node 2L can be confirmed by image pickup means arranged at the distal end portion 22.

The guide wire 9L achieves its purpose when it completes guidance for inserting the distal end portion 22 into the mediastinum 3. Accordingly, the operator may pull out the guide wire 9L from a channel 23. Then, the operator may insert a treatment instrument for endoscope to be used at an incision step, through the channel 23.

<Step S49> Separation Step

The operator cuts off the lymph node 2L from the surrounding tissue under observation on a visual field 25L of an endoscopic image picked up by the optical observation means 25. The operator may use a cut-off instrument and the like as necessary then. When the lymph node 2L is not connected with the surrounding tissue, cut-off is not necessary. It is required only to separate the lymph node 2L from the surrounding tissue.

<Step S50> Drawing-in Step

The operator draws the lymph node 2L into the esophagus 5.

<Step S51> Fistula Closing Step

This step is almost the same as the step of the lymph node removing method of the fourth embodiment.

<Step S52> Taking-out Step

This step is almost the same as the step of the lymph node removing method of the third embodiment. Similarly to the lymph node removing method of the third embodiment, the taking-out step is not an indispensable step in the lymph node removing method of the present embodiment.

As described above, according to the lymph node removing method of the present embodiment, it is possible not only to obtain operation effects similar to those of the lymph node removing method of the third embodiment and the lymph node removing method of the fourth embodiment but also certainly take out the target lymph node 2L because it is possible to insert the distal end portion 22 of the endoscope 20 into the mediastinum 3 and optically confirm target lymph node 2L.

Furthermore, in the lymph node removing method of the present embodiment, by using the guide wire 9L, which is a treatment instrument for endoscope anchored in the target lymph node 2L, the operator can insert the distal end portion up to a position where an image of the target lymph node 2L can be certainly picked.

The lymph node removing method of the present embodiment can be applied not only to remove of a lymph node but also to remove of a lymph node tissue.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A lymph node removing method comprising the steps of:
   an insertion step, wherein an endoscope has an insertable insertion portion which is inserted into an esophagus or a trachea being a lumen inside the body of a subject; the step of inserting a distal end portion arranged at the tip of the insertion portion of the endoscope into the lumen;
   a confirmation step of confirming the position of a lymph node located outside the lumen by performing ultrasound scanning using an ultrasound transducer arranged at the distal end portion of the endoscope;
   an anchoring step of sticking a distal end of an anchoring device which has been inserted through a channel inside the insertion portion into a wall of the lumen so as to penetrate through the wall and placing the distal end of the anchoring device on the lymph node while performing the ultrasound scanning;
   an incision step of cutting the wall of the lumen to make a fistula for drawing the lymph node into the lumen, after placing the distal end of the anchoring device on the lymph node; and
   a drawing-in step of drawing the lymph node through the fistula and into the lumen in which the distal end portion of the endoscope is positioned with the anchoring device.

2. The lymph node removing method according to claim 1, wherein the anchoring device is a treatment instrument for endoscope which includes a guide wire including at a distal end portion thereof a puncture needle having a barb.

3. The lymph node removing method according to claim 2, wherein the treatment instrument for endoscope comprises a barb protecting mechanism which disables the operation of the barb.

4. The lymph node removing method according to claim 1, further comprising a fistula closing step of closing the fistula after the drawing-in step.

5. The lymph node removing method according to claim 4, further comprising a closing device placing step of placing a fistula closing device on the luminal wall after the confirmation step and before the anchoring step; wherein
   the fistula closing step is performed with the use of the fistula closing device.

6. The lymph node removing method according to claim 1, further comprising a separation step of separating the lymph node from a surrounding tissue after the drawing-in step.

7. A lymph node removing method comprising the steps of:
an insertion step, wherein an endoscope has an insertable insertion portion which is inserted into an esophagus or a trachea being a lumen inside the body of a subject; the step of inserting a distal end portion arranged at the tip of the insertion portion of the endoscope into the lumen;
a confirmation step of confirming the position of the lymph node located outside the lumen by performing ultrasound scanning using an ultrasound transducer arranged at the distal end portion of the endoscope;
an anchoring step of sticking a distal end of an anchoring device which has been inserted through a channel inside the insertion portion into a wall of the lumen so as to penetrate through the wall and placing the distal end of the anchoring device on the lymph node while performing the ultrasound scanning;
an incision step of cutting the wall of the lumen to make a fistula for drawing the lymph node into the lumen, after placing the distal end of the anchoring device on the lymph node; and
an insertion-into-mediastinum step of inserting the distal end portion of the endoscope from the fistula into a mediastinum using the anchoring device as a guide;
a separation step of separating the lymph node from a surrounding tissue under observation on an endoscopic image picked up by an image pickup device arranged at the distal end portion of the endoscope; and
a drawing-in step of drawing the lymph node through the fistula and into the lumen in which the distal end portion of the endoscope is positioned.

8. The lymph node removing method according to claim 7, wherein the anchoring device is a treatment instrument for endoscope which includes a guide wire including at a distal end portion thereof a puncture needle having a barb.

9. The lymph node removing method according to claim 8, wherein the treatment instrument for endoscope comprises a barb protecting mechanism which disables the operation of the barb.

10. The lymph node removing method according to claim 7, further comprising a fistula closing step of closing the fistula after the drawing-in step.

11. The lymph node removing method according to claim 10, further comprising a closing device placing step of placing a fistula closing device on the luminal wall after the confirmation step and before the anchoring step; wherein
the fistula closing step is performed with the use of the fistula closing device.

12. A lymph node removing method comprising the steps of:
an insertion step, wherein an endoscope has an insertable insertion portion which is inserted into an esophagus or a trachea being a lumen inside the body of a subject; the step of inserting a distal end portion arranged at the tip of the insertion portion of the endoscope into the lumen;
a confirmation step of confirming the position of a lymph node by performing ultrasound scanning using an ultrasound transducer arranged at the distal end portion of the endoscope;
an anchoring step of placing a distal end of an anchoring device which has been inserted through a channel inside the insertion portion, on the lymph node while performing the ultrasound scanning;
an incision step of drawing out at least one flexible wire electrode from a circumference part of the distal end portion of the insertion portion of the endoscope in a radial direction of the distal end portion to place the at least one flexible wire electrode in contact with a wall of the lumen, and actuating the at least one flexible wire electrode to perform electrification of the wall of the lumen to cut the wall of the lumen to make a fistula, after placing the distal end of the anchoring device on the lymph node; and
a drawing in step of drawing the lymph node through the fistula and into the lumen with the anchoring device.

13. The lymph node removing method according to claim 12, wherein the anchoring device is a treatment for endoscope which includes a guide wire including at a distal end portion thereof a puncture needle having a barb.

14. The lymph node removing method according to claim 13, wherein the treatment instrument for endoscope comprises a barb protecting mechanism which disables the operation of the barb.

15. The lymph node removing method according to claim 12, further comprising a fistula closing step of closing the fistula after the drawing in step.

16. The lymph node removing method according to claim 15, further comprising a closing device placing step of placing a fistula closing device on the luminal wall after the confirmation step and before the anchoring step; wherein
the fistula closing step is performed with the use of the fistula closing device.

* * * * *